(12) United States Patent
Kuhn et al.

(10) Patent No.: US 6,399,810 B1
(45) Date of Patent: Jun. 4, 2002

(54) PROCESS FOR THE PREPARATION OF METHYL CYCLOHEXYL-PROPIONATE

(75) Inventors: Walter Kuhn, Holzminden; Hans-Ulrich Funk, Lauenförde; Gerhard Senft, Holzminden; Wolfgang Kiel, Odenthal, all of (DE)

(73) Assignee: Haarmann & Reimer GmbH, Holzminden (DE)

( * ) Notice: Subject to any disclaimer, the term of this patent is extended or adjusted under 35 U.S.C. 154(b) by 0 days.

(21) Appl. No.: 09/639,281

(22) Filed: Aug. 15, 2000

(30) Foreign Application Priority Data

Aug. 20, 1999 (DE) .......................................... 199 39 544

(51) Int. Cl.$^7$ .............................................. C07C 69/74
(52) U.S. Cl. ........................... 560/125; 560/1; 560/103; 560/105
(58) Field of Search ........................... 560/1, 105, 103, 560/127

(56) References Cited

U.S. PATENT DOCUMENTS

| 5,286,898 A | 2/1994 | Gustafson et al. | .......... 560/127 |
| 5,319,129 A | 6/1994 | Gustafson et al. | .......... 560/127 |

OTHER PUBLICATIONS

Cerveny et al, Czech. Rep. Perfum. Flavor, 25 (1) pp19–23, 2000.*
Sabatier et al, Comptes Rendusdes Seances 156, pp751–753, 1913.*

Cerveny, Libor, The Synthesis of Allyyl–3–Cyclohexylpropionate, Institute of Chemical Technology, Prague, Czech. Rep., Perf.um. Flavor. vol. 25, (1) pp. 19–23, 2000.*

Sabatier, Paul,Hydrogenation directe des ethers Hydrocinnamiques.. Comptes Rendusdes Seances, vol. 156, pp. 751–753, 1913.*

Fache, Fabienne, A Catalytic Stereo– and Chemo–selective method for the Reduction of Substituted Aromatics, Tetrahedron Letters vol. 36, No. 6, pp. 885–888, 1995.*

Chemical Abstracts, vol. 132, No. 22, May 29, 2000, Columbus, Ohio, US; abstract No. 293517t.

Cerveny Libor et al,: The Synthesis of Allyl–3–Cyclohexylpropionate, Seite 667; Spalte r; XP002158953, *Zusammenfassung* & Cerveny Libor et al: Perfum. Flavor, Bd. 25, Nr. 1, 2000, Seiten 19–23.

* cited by examiner

Primary Examiner—Gary Geist
Assistant Examiner—Hector M Reyes
(74) Attorney, Agent, or Firm—Joseph C. Gil; Noland J. Cheung

(57) ABSTRACT

Methyl cyclohexyl-propionate is prepared by the hydrogenation of methyl cinnamate in the presence of a ruthenium and/or palladium catalyst.

4 Claims, No Drawings

PROCESS FOR THE PREPARATION OF METHYL CYCLOHEXYL-PROPIONATE

FIELD OF THE INVENTION

The invention relates to a process for the preparation of methyl cyclohexyl-propionate in the presence of a ruthenium and/or palladium catalyst starting with methylcinnamate.

BACKGROUND OF THE INVENTION

C. R. Hebd. Seances Acad. Sci. 1913, 156, 751 to 753 describes the hydrogenation of methyl cinnamate to give methyl cyclohexyl-propionate under Raney nickel catalyst at 170 to 185° C. Increasing the temperature to 200° C. results in ester cleavage and deactivation of the Raney nickel catalyst. The methyl cyclohexyl-propionate produced using the process has insufficient purity.

SUMMARY OF THE INVENTION

The object of the present invention was to prepare methyl cyclohexyl-propionate in high purity.

We have found a process for the preparation of methyl cyclohexyl-propionate by hydrogenation of methyl cinnamate in the presence of a catalyst, which is characterized in that a ruthenium and/or palladium catalyst is used.

DETAILED DESCRIPTION OF THE INVENTION

Ruthenium and palladium catalysts are known per se (Methoden der organischen Chemie [Methods in Organic Chemistry]/Houben Weyl, Volume IV/1c, Reduction Part 1, Georg Thieme Verlag, Stuttgart, 1980, pages 15 to 562, Handbook of Heterogeneous Catalysis, Vol. 1–5, pages 2123 to 2447; V C H Weinheim; 1997).

The catalysts are usually applied to a support. Examples of suitable supports are activated carbon, silicon dioxide, calcium carbonate, and aluminum oxide. The preferred support is activated carbon.

The support for the process according to the present invention generally comprises from 1 to 20% by weight, preferably from 5 to 10% by weight, of ruthenium and/or palladium, based on the overall catalyst.

It is also possible to use mixed catalysts of ruthenium and palladium.

For the process according to the present invention, the catalyst can be used in the dry or moist state (up to 60% of water).

For the process according to the present invention, the weight ratio of the catalyst used to methyl cinnamate is from 0.0001:1 to 0.1:1, preferably from 0.005:1 to 0.05:1.

The reaction temperature for the process according to the present invention is from 30 to 250° C., preferably 60 to 200° C.

The hydrogen pressure is from 1 to 100 bar, preferably from 10 to 20 bar.

The reaction time is from 2 to 100 hours, preferably 5 to 40 hours.

The process according to the present invention can be represented by the following reaction equation:

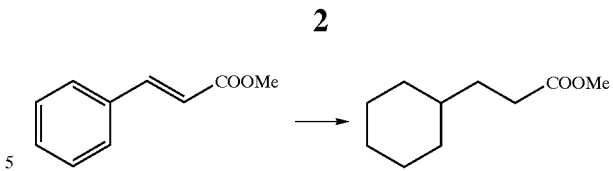

The process according to the present invention is generally carried out as follows:

The pressure container fitted with stirrer is charged with the methyl cinnamate and the catalyst. Hydrogenation is carried out at the chosen reaction temperature and hydrogen pressure. The resulting methyl cyclohexyl-propionate is obtained following removal of the catalyst by filtration, decantation or centrifugation.

In the process according to the present invention, methyl cyclohexyl-propionate is produced in a purity of >99.5% and a yield of about 99%.

Methyl cyclohexyl-propionate is a fragrance having a fruity character, which is simultaneously also a starting material for the preparation of allyl cyclohexyl-propionate. Allyl cyclohexylpropionate is a fragrance with a strong pineapple odor (S. Arctander, Perfume and Flavor Chemicals, No. 77, 1969).

Methyl cinnamate for the process according to the present invention can be prepared by esterification of cinnamic acid with methanol or by Claisen condensation of benz-aldehyde and methyl acetate (K. Bauer, D. Garbe, Fragrance and Flavor Materials, page 80, Weinheim, V C H Verlagsgesellschaft, 1985).

EXAMPLES

Example 1

A 5 l stirred autoclave fitted with a gas-dispersion stirrer is charged with 1,565 g of methyl cinnamate and 10.3 g of 5% by weight ruthenium on activated carbon in the moist state. Hydrogenation is carried out for 6 hours at 155° C. and 20 bar. Following filtration, 1,625 g of methyl cyclohexyl-propionate with a purity of 99.6% by weight are obtained. The resulting methyl cyclohexyl-propionate can be distilled without residue at a liquid-phase temperature of 135° C. and a vacuum of 35 mbar. The theoretical yield is 99%.

Example 2

A 5 l stirred autoclave fitted with a gas-dispersion stirrer is charged with 2,000 g of methyl cinnamate and 19 g of 5% by weight palladium on activated carbon in the moist state. Hydrogenation is carried out for 35 hours at 160 to 170° C. and 20 bar. Following filtration, 2,050 g of methyl cyclohexyl-propionate with a purity of 99.7% are obtained. The resulting methyl cyclohexyl-propionate can be distilled without residue at a liquid-phase temperature of 135° C. and a vacuum of 35 mbar. The theoretical yield is 98%.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of methyl cyclohexylpropionate comprising the step of hydrogenating methyl cinnamate in the presence of a ruthenium and/or palladium catalyst.

2. A process according to claim 1, wherein the weight ratio of the catalyst used to methyl cinnamate is from 0.0001:1 to 0.1:1.

3. A process according to claim 1, wherein the reaction temperature is in the range from 30 to 250° C.

4. A process according to claim 1, wherein the process is carried out at a hydrogen pressure of from 1 to 100 bar.

* * * * *